United States Patent
Ott et al.

(10) Patent No.: US 7,353,179 B2
(45) Date of Patent: Apr. 1, 2008

(54) SYSTEM AND METHOD FOR HANDLING THE ACQUISITION AND ANALYSIS OF MEDICAL DATA OVER A NETWORK

(75) Inventors: James E. Ott, Kirkwood, MO (US); Steven M. Kidder, Oak Creek, WI (US); Michael R. Buchanan, St. Peters, MO (US)

(73) Assignee: Biomedical Systems, St. Louis, MO (US)

( * ) Notice: Subject to any disclaimer, the term of this patent is extended or adjusted under 35 U.S.C. 154(b) by 380 days.

(21) Appl. No.: 10/294,541

(22) Filed: Nov. 13, 2002

(65) Prior Publication Data

US 2004/0093239 A1 May 13, 2004

(51) Int. Cl.
*A61B 5/00* (2006.01)
(52) U.S. Cl. .......................................... 705/3; 600/300
(58) Field of Classification Search ................ 705/2–3; 600/300

See application file for complete search history.

(56) References Cited

U.S. PATENT DOCUMENTS

| | | | |
|---|---|---|---|
| 5,339,821 A | 8/1994 | Fujimoto | |
| 5,544,649 A | 8/1996 | David et al. | |
| 5,544,661 A | 8/1996 | Davis et al. | |
| 5,867,821 A * | 2/1999 | Ballantyne et al. | 705/2 |
| 5,944,659 A | 8/1999 | Flach et al. | |
| 5,987,519 A * | 11/1999 | Peifer et al. | 709/230 |
| 5,997,476 A * | 12/1999 | Brown | 600/300 |
| 6,024,699 A | 2/2000 | Surwit et al. | |
| 6,039,688 A * | 3/2000 | Douglas et al. | 600/300 |
| 6,064,906 A | 5/2000 | Langberg et al. | |
| 6,101,478 A * | 8/2000 | Brown | 705/2 |
| 6,108,800 A | 8/2000 | Asawa | |
| 6,176,826 B1 | 1/2001 | Shimura et al. | |
| 6,283,761 B1 * | 9/2001 | Joao | 434/236 |
| 6,327,594 B1 * | 12/2001 | Van Huben et al. | 707/200 |
| 6,364,834 B1 | 4/2002 | Reuss et al. | |
| 6,454,705 B1 * | 9/2002 | Cosentino et al. | 600/300 |
| 6,561,975 B1 | 5/2003 | Pool et al. | |
| 6,579,242 B2 | 6/2003 | Bui et al. | |
| 6,602,191 B2 | 8/2003 | Quy | |
| 6,622,045 B2 | 9/2003 | Snell et al. | |
| 6,681,003 B2 | 1/2004 | Linder et al. | |
| 6,701,184 B2 | 3/2004 | Henkin | |
| 6,708,057 B2 | 3/2004 | Morganroth | |
| 6,749,566 B2 | 6/2004 | Russ | |
| 2001/0007053 A1 | 7/2001 | Bardy | |

(Continued)

*Primary Examiner*—Zeender Ryan Florian
*Assistant Examiner*—Vanel Frenel
(74) *Attorney, Agent, or Firm*—Senniger Powers

(57) ABSTRACT

A central server controls the receipt and analysis of patient medical data and patient information. The central server receives patient medical data and patient information from a remote computer. A storage system stores the received patient medical data, patient information, and the associated medical report prepared at analysis workstations at any location after analysis of the patient medical data. A processor controls access to and analysis of the patient medical data by analysis workstations and controls access to the medical report. The central server transmits the patient medical data to and receives the associated medical report from analysis workstations. The central server transmits the medical report associated with the patient medical data to the remote computer. Also, a method controls the acquisition and analysis of patient medical data over a network by a central server from a remote computer operably interconnected by the network with the central server.

24 Claims, 8 Drawing Sheets

U.S. PATENT DOCUMENTS

| | | |
|---|---|---|
| 2001/0044588 A1* | 11/2001 | Mault .......................... 600/549 |
| 2001/0051881 A1* | 12/2001 | Filler ........................... 705/3 |
| 2002/0013716 A1 | 1/2002 | Dunham et al. |
| 2002/0016719 A1 | 2/2002 | Nemeth et al. |
| 2002/0019745 A1 | 2/2002 | Yamigiwa et al. |
| 2002/0025336 A1* | 2/2002 | McGuire et al. ............ 424/405 |
| 2002/0035336 A1 | 3/2002 | Henkin |
| 2002/0046047 A1* | 4/2002 | Budd ............................ 705/1 |
| 2002/0082867 A1* | 6/2002 | MacCarter et al. ............ 705/2 |
| 2002/0143372 A1 | 10/2002 | Snell et al. |
| 2002/0181680 A1 | 12/2002 | Linder et al. |
| 2002/0183599 A1* | 12/2002 | Castellanos ................. 600/300 |
| 2002/0184055 A1* | 12/2002 | Naghavi et al. ............... 705/2 |
| 2002/0198473 A1* | 12/2002 | Kumar et al. ................ 600/595 |
| 2003/0004758 A1* | 1/2003 | Luttrell .......................... 705/3 |
| 2003/0028442 A1 | 2/2003 | Wagstaff et al. |
| 2003/0032991 A1 | 2/2003 | Poore |
| 2003/0045787 A1 | 3/2003 | Schulze et al. |
| 2003/0200114 A1 | 10/2003 | Ogino et al. |
| 2004/0025030 A1 | 2/2004 | Corbett-Clark et al. |
| 2004/0039264 A1 | 2/2004 | Bardy |
| 2004/0088027 A1 | 5/2004 | Burnes et al. |
| 2004/0088374 A1 | 5/2004 | Webb et al. |
| 2004/0093239 A1 | 5/2004 | Ott et al. |
| 2005/0177400 A1* | 8/2005 | Rosenfeld et al. ............. 705/3 |

* cited by examiner

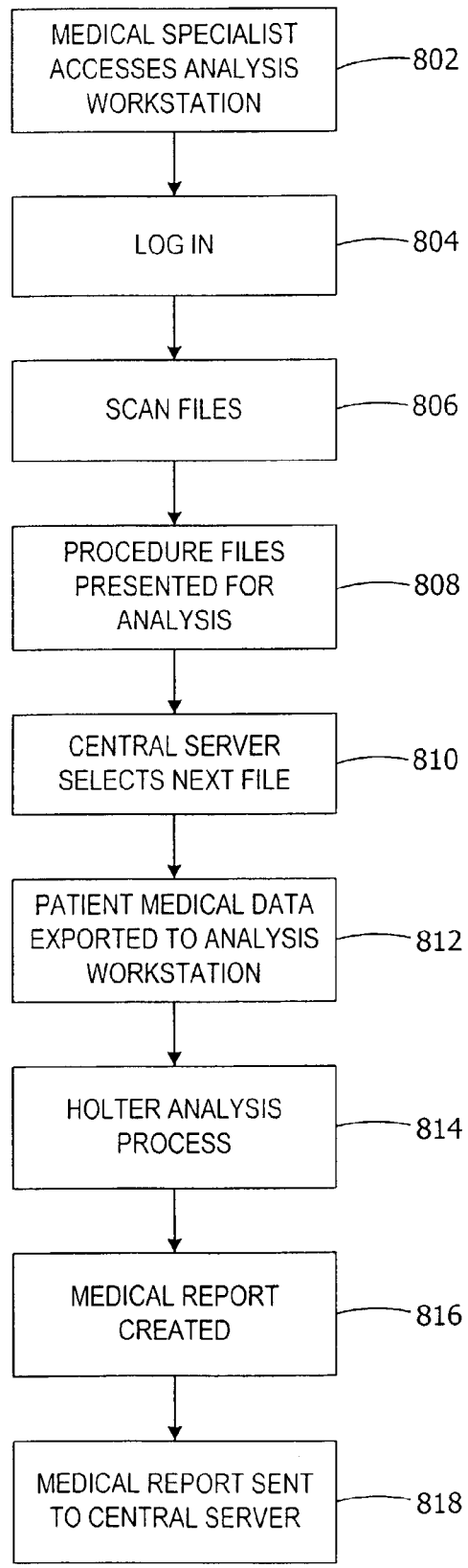

SYSTEM AND METHOD FOR HANDLING THE ACQUISITION AND ANALYSIS OF MEDICAL DATA OVER A NETWORK

FIELD OF THE INVENTION

The invention relates generally to a system and method for handling medical data on a network. In particular, the invention includes uploading patient medical data and patient information to a central server for selective access by a workstation for analyzing the patient medical data and preparing a medical report associated with the patient medical data.

BACKGROUND OF THE INVENTION

Medical devices such as medical sensors are used both in medical institutions and at home to monitor one or more vital signs or to observe and record patient medical data. The medical data is transported to medical personnel who are often specialists and have the expertise to analyze the medical data and to prepare a medical report associated with the medical data. In some instances, the medical personnel use specialized systems, methods, test systems, expert workstations and/or software to aid in the analysis of the patient medical data and in the preparation of a medical report which analyzes the patient medical data.

To accomplish this, the medical data must be readily available to the medical specialists. However, often the patient and medical data are located in remote locations away from the location of an available medical specialist. One solution is for the medical specialist to travel to the remote location such as a remote medical facility, hospital, or doctor's office to gain access to the patient medical data and to analyze the report. In other cases, the medical data is obtained at the remote facility and shipped via mail or courier service to medical facility or medical specialist located at a remote location. However, these processes are both costly and time consuming and are not desirable when the timely analysis of the patient medical data is critical to providing timely medical care to patients who may have a severe or life threatening condition.

Additionally, there are systems for remotely monitoring medical data from a patient by a medical care provider. In one such system, U.S. Pat. No. 5,339,821, issued to Fujimoto, a home medical system allows any patient to measure his or her daily condition at home and undergo a check or an inquiry diagnosis by a medical specialist or doctor located at a remote medical facility. Other systems such as U.S. Pat. No. 5,544,649, issued to David et al., provide an interactive remote patient monitoring system. However, these direct transactions often are unreliable due to the insecure nature of the transmission, the large amount of data required to be transmitted, and/or the need to associate patient information with the patient medical data and subsequently with the medical report associated with the patient medical data. Furthermore, these systems are administratively challenging and do not provide for control and management of the access to and the analysis of the patient medical data by medical specialists.

Therefore, it is desirable to have a system and method of sensing and acquiring patient medical data at a remote location for analysis by a medical specialist who is located at a remote distance. Such a system would control access to the patient medical data by the medical specialist who performs medical analysis of the patient medical data. Based on the patient medical data, the medical specialist working at an analysis workstation prepares a medical report associated with the patient medical data. The medical report is selectively provided to the remote location for review and access by local medical personnel or by the patient.

BRIEF DESCRIPTION OF THE INVENTION

In one form, the invention is a central server configured to control the receipt and analysis of patient medical data and patient information. Selective access to the patient medical data is provided to an analysis workstation that is responsive to a medical specialist. The analysis workstation analyzes the patient medical data and prepares a medical report associated with the patient medical data. A first communication interface receives patient medical data and patient information from a remote computer and transmits the medical report associated with the patient medical data to the remote computer. A storage system stores the received patient medical data, patient information, and the associated medical report. A processor is configured to control access to and analysis of the patient medical data by the analysis workstation and the medical specialist and is configured to control access to the medical report. A second communication interface transmits the patient medical data to the analysis workstation and receives the associated medical report from the analysis workstation.

In another form, the invention is a system for handling patient medical data over a network. A remote computer is configured to receive patient medical data from a medical sensor. The remote computer is further configured to transfer the received patient medical data and patient information corresponding to the patient medical data. A central server is configured to receive and store the transferred patient medical data and corresponding patient information and is further configured to control access to the patient medical data and its corresponding patient information. An analysis workstation is associated with the central server. The analysis workstation is operated by a medical specialist who accesses and analyzes the patient medical data stored on the central server. The analysis workstation is responsive to the medical specialist to create a medical report associated with the patient medical data and transmits the medical report to the central server. The central server is also configured to receive from the analysis workstation the medical report associated with the patient medical data and corresponding patient information, and is configured to transmit the medical report to the remote computer.

In yet another form, the invention is a method of controlling the acquisition and analysis of patient medical data over a network by a central server from a remote computer operably interconnected by the network with the central server. The method comprises receiving at a central server patient medical data and corresponding patient information from the remote computer. The central server controls access to and analysis of the received patient medical data by providing secure access by an analysis workstation. The patient medical data is transferred to an analysis workstation that is responsive to the medical specialist for analyzing the medical data and for creating a medical report associated with the patient medical data. The medical report is transferred to the central server from the analysis workstation. The central server receives from the analysis workstation the medical report associated with the patient medical data and corresponding patient information. The central server transmits the medical report to the remote workstation over the network.

In another form, the invention is a method for managing the receipt and analysis of Holter monitor patient medical data received at a remote computer and analyzed by a medical specialist located at a location remote from the remote computer. The method includes recording patient medical data on a medical sensor at a remote site, storing the patient medical data on a local storage medium, and transmitting the stored patient medical data to a remote computer. At the remote computer site, patient information corresponding to the patient medical data is created. The patient medical data is received from the medical sensor and stored on the remote computer. The patient medical data is compressed and transmitted along with corresponding patient information to the central server. The central server receives the compressed patient medical data and corresponding patient information, decompresses the patient medical data and stores the patient medical data and patient information. The central server controls access to the patient medical data and patient information. The patient medical data is transferred to an analysis workstation, which receives the patient medical data from the central server. The analysis workstation analyzes the patient medical data and generates a medical report associated with medical data. The medical report is transferred to the central server where it is received. The central server stores the medical report and controls access to the medical report. The medical report is transmitted to the remote computer where it is received from the central server and displayed.

The system and method of the present invention has a number of advantages over the prior art. The present system provides for remote acquisition of patient medical data and patient information at a local easily accessible medical facility or possibly at home. The patient medical data and patient information is transmitted to a central server that controls the receipt of and access to the patient medical data. The central server selectively provides the patient medical data to medical specialists who use an analysis workstation to analyze the patient medical data and prepare a medical report. Access to the medical reports are controlled by the central server and provided to the remote computer at the remote location for receipt and review by the local medical provider or the patient. Such a system provides a secure, timely and efficient acquisition and analysis of patient medical data that is not provided by prior art systems.

Other aspects and forms of the invention will be in part apparent and in part pointed out hereinafter.

BRIEF DESCRIPTION OF THE DRAWINGS

FIG. 8 is a block diagram illustrating a method of an analysis workstation accessing the patient medical data and the creation of a medical report associated with the patient medical data according to one form of the invention.

Corresponding reference characters and designations generally indicate corresponding parts throughout the drawings.

DETAILED DESCRIPTION

Figure 1:
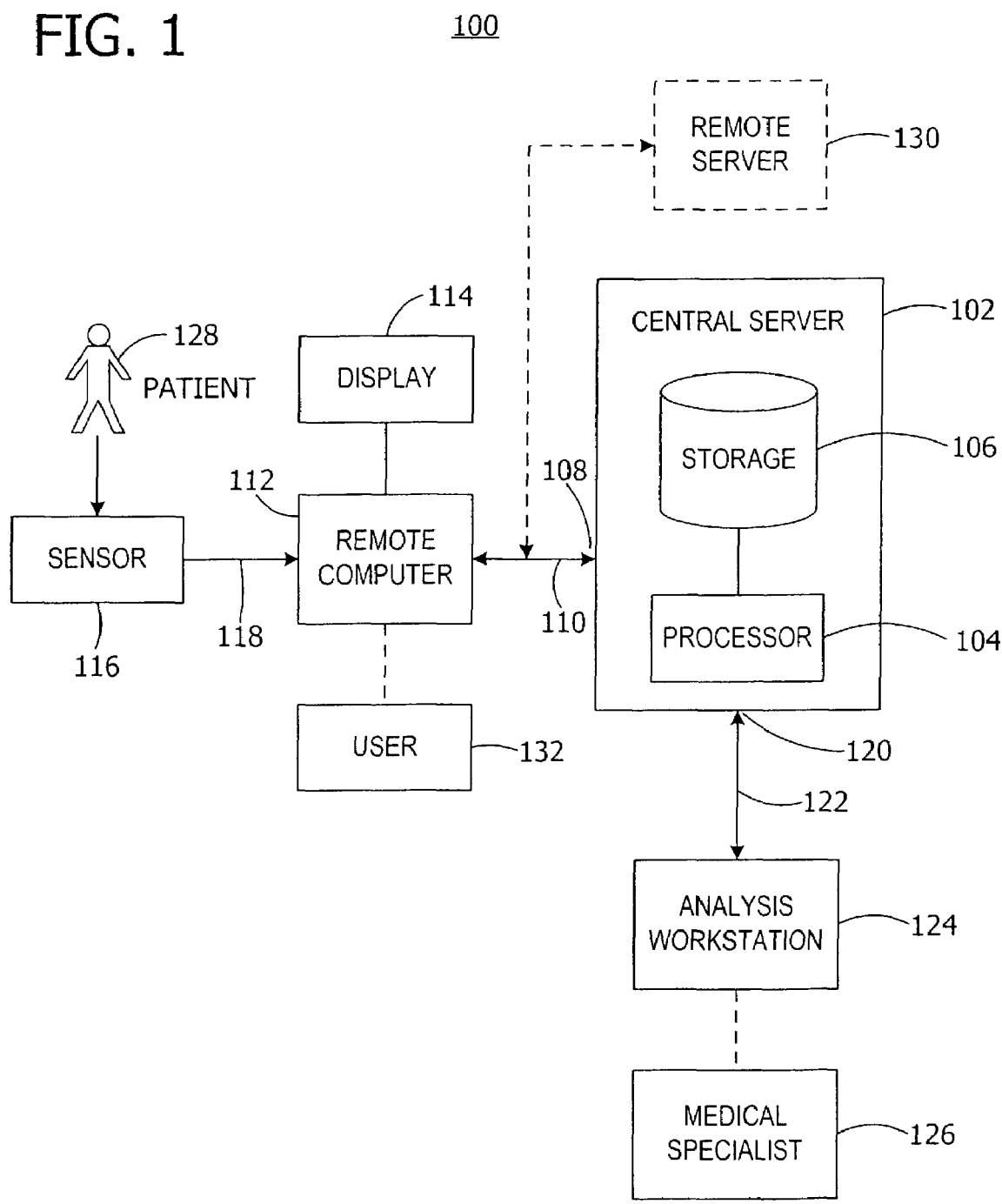
FIG. 1 is a diagram illustrating a central server with optional remote server for handling the acquisition and analysis of patient medical data over a network according to one preferred embodiment of the invention.

Referring now to FIG. 1, one preferred embodiment of a system 100 for handling the acquisition and analysis of patient medical data and patient information over a network is illustrated. Patient information is specific data such as name, address, contact information, patient medical history, medical care provider information, and medical insurance data associated with a patient 128. Patient medical data is medical data associated with one or more body functions of the patient 128 that have been measured and recorded.

The system 100 includes a central server 102 with a processor 104 and a storage system 106. The processor 104 is configured to associate the patient medical data with the patient information. The storage system 106 may be any storage system such as local memory, fixed storage disks, remote storage disks, a database, or otherwise configured to store patient medical data, patient information and/or medical reports.

The server 102 includes a first communications interface 108 or other input/output port that is connected to a first communication network 110. A remote computer 112 is equipped with a display 114 and is connected to the first network 110. A medical sensor 116 provides patient medical data to the remote computer 112 via a data transfer system or connection 118. The remote computer 112 is responsive to a user 132, which may be a patient 128 or medical personnel located at a remote medical facility or doctor's office. The remote computer 112 is configured with a patient medical data acquisition, compression and transmission program for receiving patient medical data from the sensor 116, for storing the patient medical data in its memory, for segmenting and compressing the patient medical data into one or more separate files, and for transferring the segmented and compressed patient medical data from the remote computer 112 to the central server 102 via first network 110. The patient medical data acquisition, compression and transmission program may be stored via a local program load function in a memory of the remote computer 112 or may be downloaded to the remote computer 112 from a remote location over the first network 110. The first communication interface 108 receives the patient medical data and the patient information from the remote computer 112 over the first network 110.

As shown in FIG. 1, the sensor 116 senses a parameter of a patient's body and stores data corresponding to the sensed parameter as patient medical data. The sensor 116 records the patient medical data recorded by the sensor 116 and stores the patient medical data in a local storage mechanism (not shown). This sensor storage mechanism may be local memory or may be a fixed or removable storage medium such as a PCMCIA flash card. The sensor 116 may be a Holter monitor or recorder that records electrocardiogram (ECG) data of the patient 128 over a period of time. For example, the Holter monitor records ECG data or Holter data over a period of 24 hours. The Holter monitor is equipped with internal memory for storing the Holter data (not shown). The sensor 116 is equipped with a communication interface configured to download or transmit the stored patient medical data from the sensor 116 to the remote computer 112 via a data transfer system 118 that is compatible with the communication interface of the remote computer 112. For example, the communication interface may be a Universal Serial Bus (USB) interface that is commonly found on a personal computer. In such an arrangement, the remote computer 112 includes a USB interface such that the sensor 116 transfers the patient medical data from its USB interface over the data transfer system 118 to the USB interface of the remote computer 112. The data transfer system 118 may be any type for transferring data such as a serial interface, a parallel interface, a local area network interface, an infrared interface, an optical interface, or other hard-wired or wireless interface.

The data transfer system 118 may also be a removable storage medium or mechanism for storage of the patient medical data. One such removable storage medium is a PCMCIA flash card. The sensor 116 and remote computer 112 would each be configured for the PCMCIA card. Initially, the card would be positioned within the sensor 116 to store patient data being recorded by the sensor 116. After recording and storage are completed, the PCMCIA flashcard with the stored patient medical data from the sensor 116 is removed from the sensor 116 and inserted into the PCMCIA slot of the remote computer 112. The patient medical data is removed, copied or transferred by the remote computer 112 to its memory for segmentation and compression. In an alternative embodiment, the PCMCIA card may itself be equipped with the USB interface and the patient medical data transferred from the PCMCIA card located in the sensor 116 via the USB interface to the remote computer 112. Other memory storage devices are also possible. For example, the sensor 116 and the remote computer 112 may be configured to store and retrieve patient medical data using a floppy disk, a CD-ROM, a memory stick, memory card or other removable storage medium.

The remote computer 112 stores the received patient medical data on its local storage medium (not shown). The remote computer 112 segments the patient medical data and compresses the segmented patient medical data for improved transmission to the central server 102. For example, patient medical data are usually large data files of more than 10 megabytes of data. The remote computer 112 may compress the patient medical data into a plurality of smaller files such as one-megabyte files. In this case, the plurality of one-megabyte files composing a single patient medical data are identified or named in such a manner as to enable their efficient and effective decompression back into the original patient medical data prior to the compression process. Additionally, the transmission of the smaller segmented and compressed data files is improved since a transmission error occurring during the transmission will only require the retransmission of a single one-megabyte files, rather than the entire patient medical data file. After segmenting and compressing, the remote computer 112 transmits the stored patient medical data over the first communication network 110 to the first communication interface 108 of the central server 102.

The first communication network 110 may be any communication network capable of transmission of data. Examples of the first network 110 include the public switched network, the public data network, a packet switched data network, an Internet, or a wireless network. The first network 110 may be the Internet capable of supporting web pages and web page communications. The remote computer 112 may be equipped with an Internet communication interface or service from an Internet Service Provider (ISP) who enables communication of data between the interconnected remote computer 112 and any other interconnected computer including the central server 102. The central server 102 is configured for communication over an operably connected communication network 110 such as the Internet. The first communication interface 108 of the central server 102 is configured to receive and transmit data from and to the remote computer 112.

The processor 104 of the central server 102 may host a web page such that the remote computer 112 located remote from the central server 102 accesses the web page. When the remote computer 112 accesses the web page hosted by the central server 102, the remote computer 112 under the control of the user 132 transmits the patient medical data and associated patient information from its memory to the central server 102 through the web page. Processor 104 receives the segmented and compressed patient medical data and associated patient information received from remote computer. The processor 104 decompresses the patient medical data and recompiles the segmented patient medical data and stores the patient medical data and patient information for controlled access and future analysis.

Optionally, a remote server 130 connected to the first network 110 between the remote computer 112 and the central server 102 may be employed. The remote server 130 hosts the web page that is accessible by the remote computer 112 configured with a web browser. The remote computer 112 transmits the patient medical data and patient information to the web page of the remote server 130. The remote server 130 transfers the received patient medical data and patient information to the central server 102 over the first network 110 to the first communication interface 108. This optional configuration allows more flexibility. For example, the remote server 130 may be hosted by an Internet Service Provider (ISP) at a central communication hub in the first network 110 and the central server 102 may be remotely located at a medical institution or medical service provider's location.

The central server 102 may receive patient medical data from a plurality of sensor 116 and/or remote computers 112 over the first network 110. While FIG. 1 only shows a single sensor 116 and a single remote computer 112, in operation a plurality of sensors would provide patient medical data to each remote computer 112. Additionally, a plurality of remote computers 112 would be located at a plurality of widely dispersed medical institutions, all of which are independently connected to the first network 110. As such, the plurality of remote computers 112 and the central server 102 communicate over the first network 110 using a secure access that is a minimum of 128-bit secure socket layer connection. In other embodiments, other secure access arrangements may also be incorporated consistent with the invention.

Referring again to FIG. 1, the central server 102 is further configured with a second communication interface 120, which is connected to a second network 122. An analysis workstation 124 is also connected to the second network 122 such that analysis workstation 124 and the central server 102 communicate by sending data files such as patient medical data from the central server 102 to analysis workstation 124. Of course, while a single analysis workstation 124 and medical specialist 126 is shown in FIG. 1, a plurality of analysis workstations 124 may be connected to the second network 122 and operable with the second communication interface 120 of the central server 102 such that more than one analysis workstation 124 is operable at any instance in time.

The processor 104 is further configured to control access to and analysis of patient medical data by the analysis workstation 124 and to control access to the medical report associated with the patient medical data and generated by the workstation 124. The medical report is stored in storage system 106 and includes data, written analysis text files, diagrams, graphs, spreadsheets, test data, objects, object files, audio files, or video files. The analysis workstation 124 is responsive to an operator such as a medical specialist 126 to receive the patient medical data, to analyze the patient medical data and to prepare the medical report associated with the patient medical data. The processor 104 controls access to the patient medical data by analysis workstation 124 for analysis by the medical specialist 126. The medical report is created by the analysis workstation 124 and is transmitted by the analysis workstation 124 to the central server over the second network 122. The processor 104 associates the medical report with the patient medical data and patient information. The processor 104 notifies remote computer 112, which is authorized to receive the particular medical report for a particular patient 128, that the medical report is complete. The user 132 of the remote computer 112 instructs the remote computer 112 to request a copy of the medical report that is controlled by the central server 102. The central server 102 transmits the medical report to the remote computer 112 which displays the medical report on the display 114, stores the medical report on a local storage medium (not shown), or prints the report on a local printer (not shown) associated with the remote computer 112. Additionally, the central server 102 transmits the medical report to the remote computer 112 over the first communication interface 108.

Figure 2:
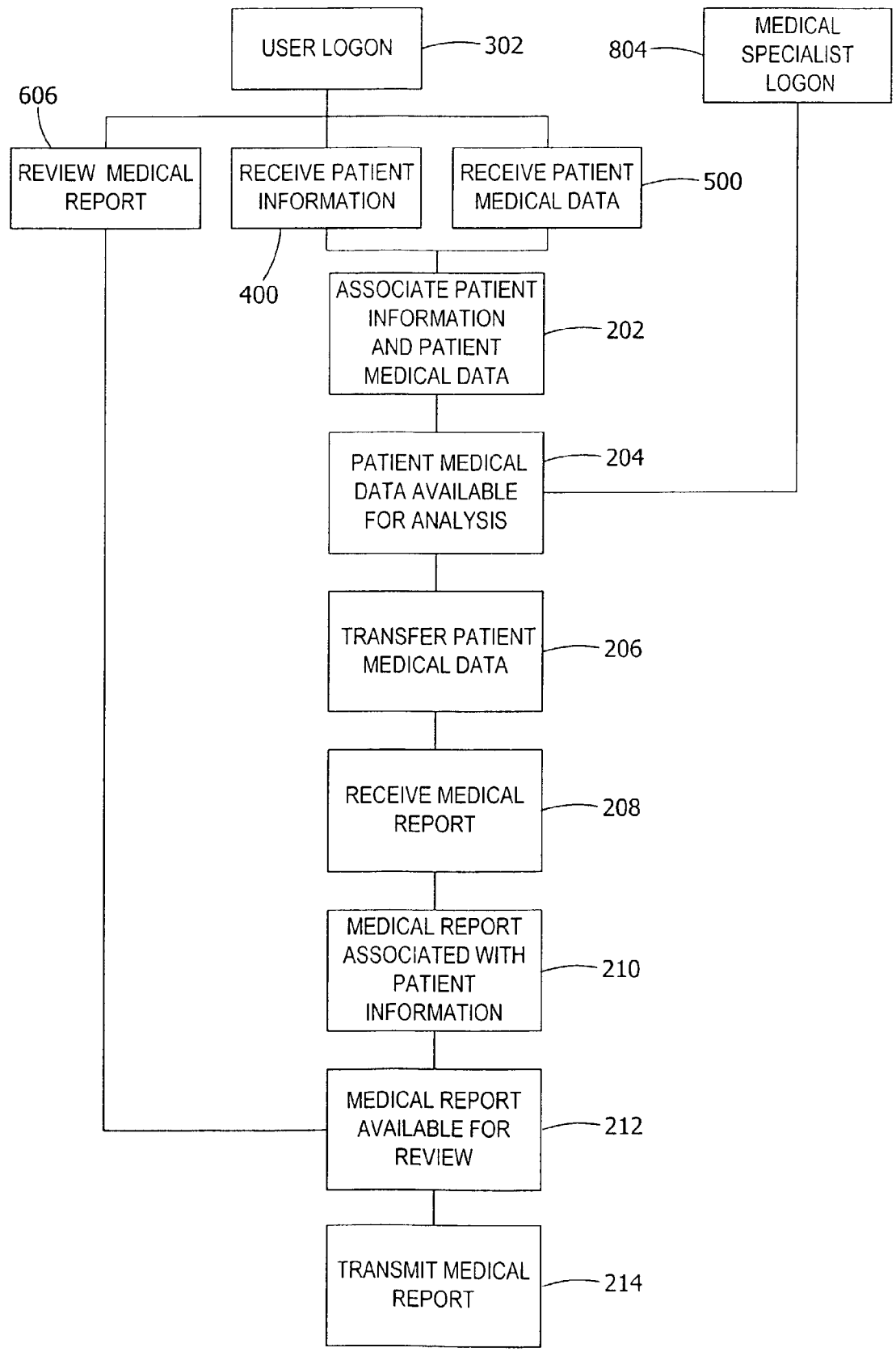
FIG. 2 is a block diagram illustrating a method of acquiring and controlling the access to and analysis of patient medical data over a network by a central server according to one form of the invention.

FIG. 2 illustrates one process for controlling analysis of patient information, patient medical data and medical reports by the central server 102. The user 132 logs into the central server 102 at 302. The central server 102 may receive patient information at 400 from the logged on user 132 or receive patient medical data at 500. The central server 102 associates the received patient medical data with patient information at 202. The patient information may be pre-existing patient information or new patient information added via 400. Next, the central server 102 makes the patient medical data available for analysis by one of the medical specialists 126 operating one of the analysis workstations 124. The medical specialist 126 logs into the central server at 804 and is notified of the available patient medical data for analysis (at 204). Once the medical specialist 126 selects a particular file or files of patient medical data to analyze, the central server 102 at 206 transfers the particular patient medical data to the analysis workstation 124 of the medical specialist 126. The central server 102 may restrict access to particular patient medical data either by a particular analysis workstation 124 or by a particular medical specialist 126. For example, the medical specialist 126 may be restricted to only receiving patient medical data for analysis from a particular group of remote computers 112 which may represent a group of medical institutions or clients. After transferring the patient report at 206, the central server 102 marks the particular patient medical data as being under analysis and restricts further access to the data by another medical specialist 126 or analysis workstation 124.

When the analysis of the patient medical data by the medical specialist 126 is complete, the medical specialist 126 instructs the analysis workstation 124 to transmit the medical report to the central server 102. The central server 102 receives and stores the medical report at 208 and associates it with the corresponding patient medical data and the patient information at 210. Once the medical report is associated with the patient information, the medical report is made available to one or more users 132 at remote computers 112 based on pre-established authorization and notification assignments at 212. The user 128 may request one of the stored medical reports at 606 using the "review results" process discussed later in FIG. 6. If the user selects to review the medical report at 606, the central server 102 transmits the medical report at 214 to the remote computer 112 associated with the requesting user 132 over the first network 110.

In operation, the medical data of the patient 128 is recorded at the site of the patient 128 with the sensor 116. A local medical care provider such as a physician at a local medical office provides the patient 128 with the sensor 116. The patient 128 uses the sensor 116 such as an electrocardiogram (ECG) data recorder or the Holter monitor/recorder to record ECG data over a defined period of time. The patient 128 wears the monitor at home or work during normal daily activity. After the defined period of time has elapsed and the recording is complete, the patient 128 returns to the medical office or facility with the sensor 116 or directly accesses a remote computer 112 equipped with the necessary acquisition software as discussed above and below. The sensor 116 has the patient medical data stored internally in memory or on a removable storage format. The user 132 of the remote computer 112 is the medical technician, medical assistant, doctor or may be the patient 128. Remote computer 112 is configured with software designed to retrieve and manage the patient medical data. As noted earlier, a software configuration consistent with this invention is the patient medical data acquisition, compression and transmission program for receiving patient medical data from the sensor 116, storing the patient medical data on the remote computer 112, compressing the medical data, and transferring the patient medical data from the remote computer 112 to the central server 102. The remote computer 112 is configured such that the storage format and patient medical data as presented by the data transfer system 118 is seen as a removable drive on the remote computer 112.

As noted above, the remote computer 112 is configured with the web browser or other data communication interface. The user 132 of the remote computer 112 logs onto the central server 102 through a secure access connection such as a secure socket layer connection with a 128-bit minimum encryption. This provides secure access to the central server 102 and the transmitted patient medical data and the patient information. The central server 102 hosts a web page and receives the patient medical data via the web page from the remote computer 112 configured with the web browser. As described above, the central server 102 transfers the patient medical data to the medical specialist 126 operating the analysis workstation 124. The analysis workstation generates the medical report associated with the patient medical data and transmits the medical report to the central server 102. The central server 102 associates the medical report with the patient information and patient medical data and provides selective access to the medical report from one or more remote computers 112 or users 132 of remote computers 112. The central server 102 transmits or provides access to the medical report by the remote computer 112 via the web page.

Figure 3:
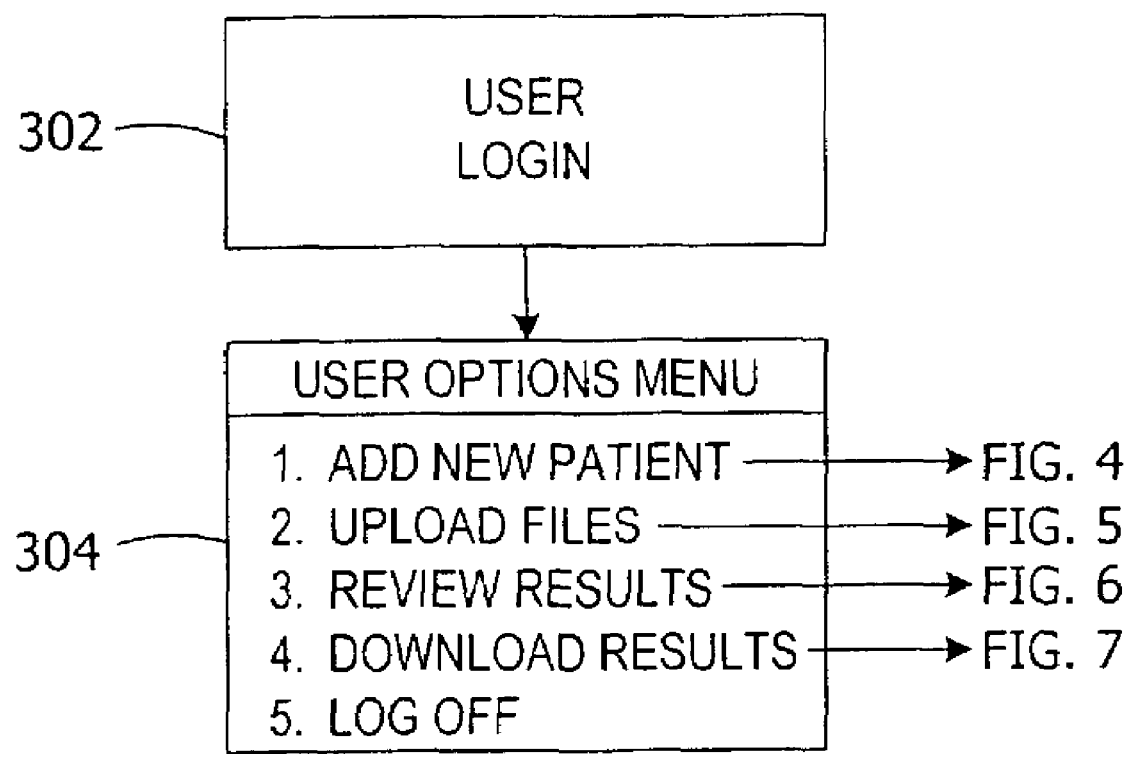
FIG. 3 is a block diagram illustrating the user options menu for initiating the acquisition and analysis of patient medical data over a network according to one form of the invention.

FIG. 3 illustrates the user login screen 302 that is presented to the user 132 of the remote computer 112 when the user 132 logs into the central server 102. Once the user 132 logs in, the user 132 is presented with a user options menu 304. The list of available options for user 132 are defined by the central server 102 based on a pre-establish list of authorized functions or activities based on the user identification number. For example, a medical assistant 132 in a medical office may operate the remote computer 112 to upload patient medical data. The medical assistant user 132 may not be authorized to view the associated medical reports once completed. However, the attending physician may be notified of the availability of the medical report, and may access the system to view the medical report. Generally, the user 132 may select one of the options from the "users option menu": (1) add new patient, (2) upload patient medical data, (3) review a medical report, (4) download a medical report, or (5) log off. FIGS. 4 to 7 illustrate processes associated with each of these user options.

Figure 4:
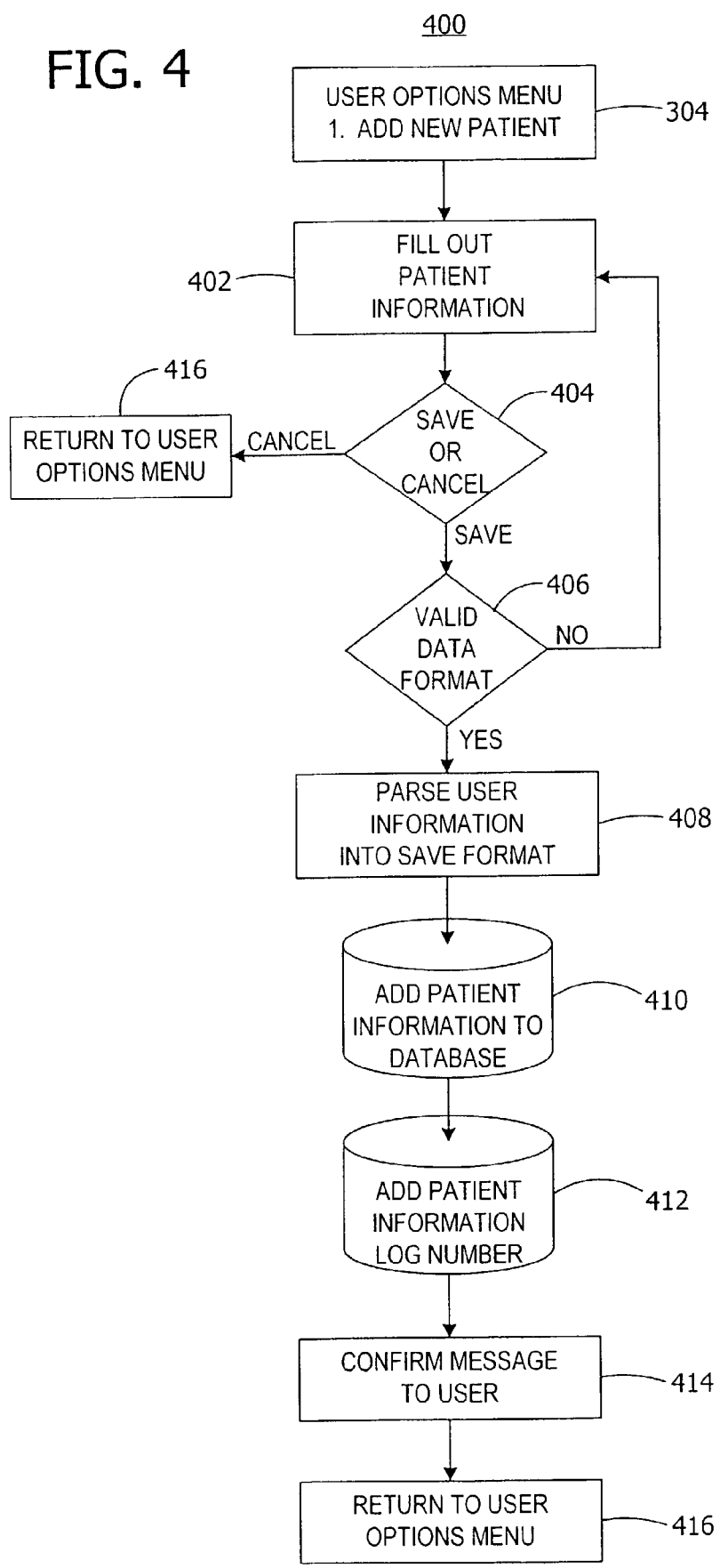
FIG. 4 is a block diagram illustrating the process of adding a new patient according to one form of the invention.

FIG. 4 illustrates the "add new patient" process 400 as selected by the user 132 on the "user options menu" 304, the user is prompted to supply the patient information at 402. The central server 102 presents the user 132 with a series of user information screens. The user 132 interacts with the web page hosted by the central server 102 or optional remote server 130 and enters the patient information. The user 132 is then requested to save or cancel the entered data at 404. If the user 132 selects to cancel, the user 132 is returned at 406 to the user options menu 304. If the user 132 selects to save, the central server 102 verifies the validity of the data format at 406. If the data is not in a valid format, the user 132 is returned to the patient entry at 416. If the data is valid, the central server 102 parses the patient information into a save format at 408 and adds the patient information to a database at 410. The method further adds a log number to the patient information at 412 when the information is stored and sends a confirmation message at 414 to the user 132. Once this is complete, the central server 102 returns the user 132 at 416 to the user options menu 304. The user 132 need only complete the "add new patient" process of 400 for a patient 128 that is new to the central server 102. If the patient information already exists in the central server 102 for a patient 128, this process is not required. At this point, the user 132 may upload the patient medical data, such as the Holter data to the central server 102 from the remote computer 112.

Figure 5:
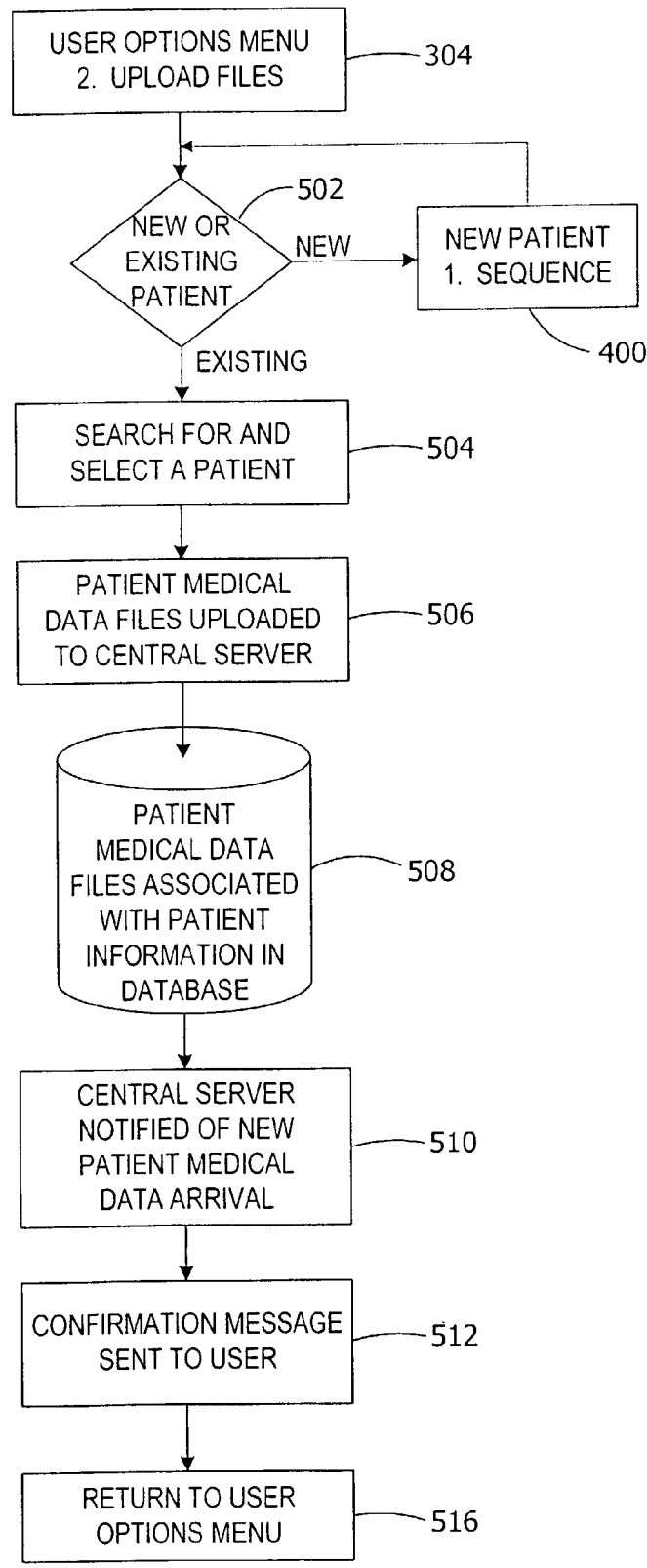
FIG. 5 is a block diagram illustrating the patient medical data upload process according to one form of the invention.

Referring now to FIG. 5, when the user 132 of the remote computer 112 selects the "upload files" process 500 from the user options menu 304, the user 132 is prompted to select either a new or existing patient 128 at 502. If a new patient 128, the user 132 is directed to the new patient sequence 400 as discussed above. If an existing patient 128, the user 132 is offered a list of patients at 504. Of course, the list of patients offered to a particular user 132 by the central server 102 is limited based on the user authorization identified when the user 132 logged into central server 201. When the user 132 selects a particular patient 128, the remote computer 112 uploads the patient medical data to the central server 102 at 506 and the central server 102 receives the uploaded files. The transmission of the patient medical data from the remote computer 112 to the central server 102 may occur immediately or may be delayed to a later time. For instance, the transmission of the patient medical data may be delayed to be sent after business hours, when the need or usage of the remote computer 112 or first network 110 is less. When the remote computer 112 has compressed the patient medical data into segmented compressed files prior to transmission to the central server 102, the central server 102 decompresses the received compressed patient medical data and recompiles the patient medical data to the state it was before being compressed by the remote computer 112. The central server 102 associates the patient medical data with the patient information and stores the patient medical data in storage 106, as discussed above and shown at 508. Once the patient medical data is stored and ready for access, the central server 102 is notified of new patient medical data at 510 and a confirmation message is sent to the user 132 at the remote computer 112 at 512. The user 132 operating the remote computer 112 is returned to the user options menu 304 at 416.

Figure 6:
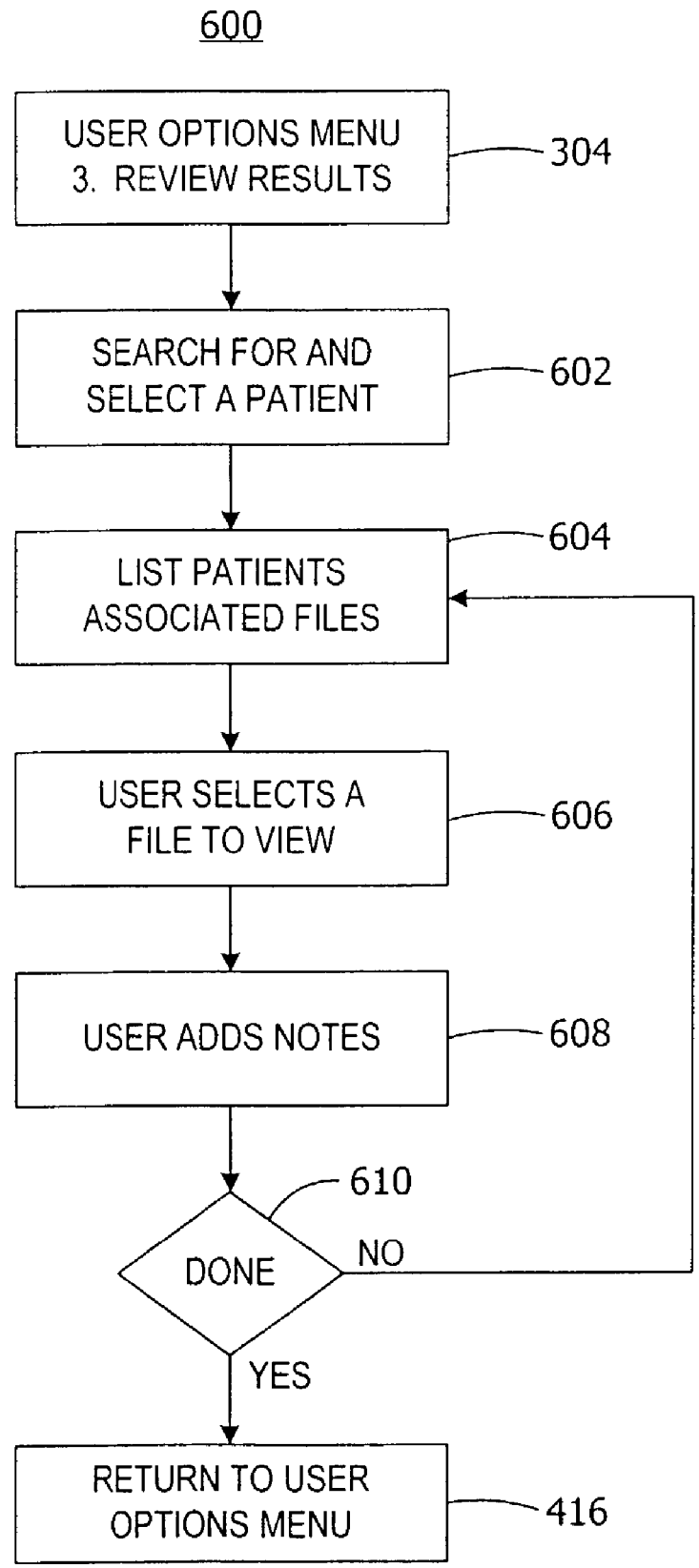
FIG. 6 is a block diagram illustrating the method of transmitting a medical report associated with patient medical data and patient information to the remote computer according to one form of the invention.

Referring now to FIG. 6, when the user 132 selects the "review results" process 600 from the user options menu 304, the user 132 of the remote computer 112 searches for a particular medical report associated with a particular patient 128 and selects the patient 128 or the medical report at 602. The central server 102 provides the remote computer 112 with a list of available completed medical reports and associated files at 604. The user 132 selects one of the available medical reports to view at 606. Once the user 132 has viewed the medical report, the user 132 may add notes to the medical report or to an associated report or file at 608. When this is complete at 610, the user 132 may choose to view another medical report or return to the user options menu 304 at 416.

Figure 7:
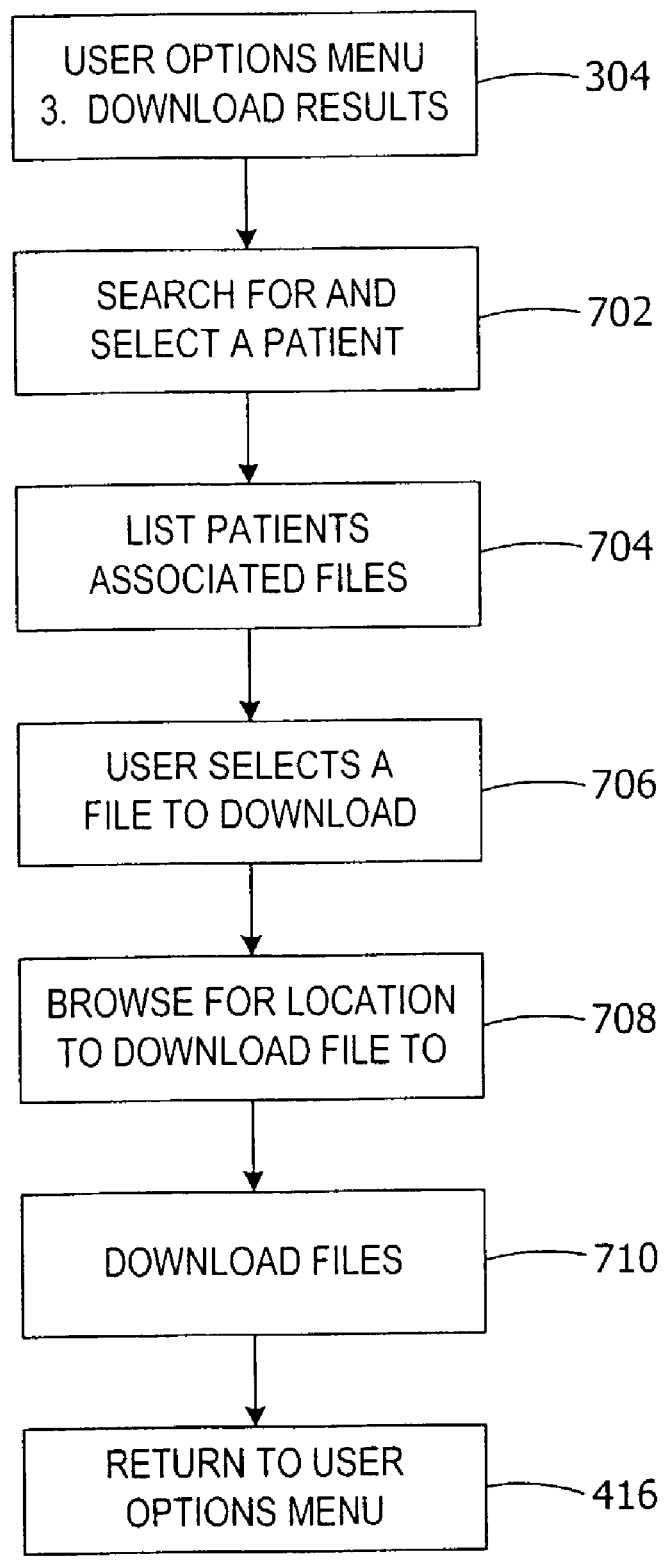
FIG. 7 is a block diagram illustrating the method of downloading a medical report associated with patient medical data and patient information to the remote computer according to one form of the invention.

Referring now to FIG. 7, when the user 132 selects the "download results" process 700 from the user options menu 304, the user 132 searches for a particular patient 128 at 702. The central server 102 lists the patients 128 available to the user 132 and the associated files at 704. From the list presented by the central server 102, the user 132 selects a file to download at 706. The user 132 selects a memory or storage location associated with the remote computer 112 to download the file to at 708 and initiates the download process. The central server 102 downloads the selected file via the first communication interface 108 over the first network 110 to the remote computer 112 at 710. Once the download has been complete, the central server 102 returns the user 132 at 416 to the user options menu 304.

The medical specialist access and analysis process 800 is illustrated in FIG. 8. The medical specialist 126, located at analysis workstation 124, logs into the central server 102 at 802. The medical specialist 126 and analysis workstation 124 are first authenticated as a valid user 132 and valid workstation at 804. An individual specialist is limited to only accessing patient medical data from certain remote computers 112 or patients 128. The central server 102 scans the system for patient medical data available to be analyzed at 806 by the particular medical specialist 126. The medical specialist 126 is presented with a list of patient medical data available to be analyzed by the particular medical specialist 126 at 808. The central server 102 provides analysis workstation 124 and the medical specialist 126 with a single patient medical data for analysis at 810. The central server 102 selectively permits a single medical specialist 126 to access a particular patient's 128 patient medical data at 812. Additionally, the central server 102 provides a patient demographic file associated with the patient medical data to analysis workstation 124. The patient demographic file is created based on the patient information received from the remote computer 112 and stored in storage 106. Analysis workstation 124, operable by the medical specialist 126, performs a medical analysis of the patient medical data at 814. The patient medical data may be Holter data from a Holter monitor and the analysis workstation 124 may be a Holter workstation configured with a Holter program to perform a Holter analysis of the Holter data. The Holter analysis results in the creation at 816 of the medical report that includes one or more data files including a Portable Document File (PDF) file containing the Holter analysis report. When the Holter analysis process and resulting medical report are complete, the medical specialist 126 logs back into the central server 102 and the central server 102 receives the completed medical report and any associated data files from analysis workstation 124 at 818. The central server 102 stores the received medical report in local memory or storage 106. The Holter report may be in a PDF file format, which is absorbed into the storage 106 as an object. Other associated files may be included in the database or stored in other storage 106 controlled by the processor 104.

When the central server 102 receives the medical report, the central server 102 notifies the associated or designated remote computer 112 that the medical report is complete and available for access and review. The remote computer 112 receives the notification and is provided access to the medical report. Controlled access by the central server 102 to the medical report is made in several different ways including viewing the report in a view mode from the remote computer 112 equipped with a web browser. Another method is for the remote computer 112 equipped with PDF-format reader, to view the document. The remote computer 112 displays the PDF-formatted medical report on display 114, stores the medical report locally, or prints the medical report on an associated printer (not shown). In another method, the medical report is transmitted as an electronic file by the central server 102 to the remote computer 112 via the first communication interface 108 over the first network 110.

The invention is also a method for managing the receipt and analysis of Holter monitor patient medical data received at the remote computer 112 and analyzed by the medical specialist 126 located at a location remote from the remote computer 112. At the site of the patient 128, patient medical data is recorded on the sensor 116 and is stored on a local storage medium. The patient medical data is transmitted to the remote computer 112. At the remote computer 112, new patient information is created that corresponds to the patient medical data. The patient medical data is received from the sensor 116 and stored on the remote computer 112. The remote computer 112 segments and/or compresses the patient medical data and transmits the segmented and/or compressed patient medical data and corresponding patient information to the central server 102.

The central server 102 receives the segmented and/or compressed patient medical data and corresponding patient information. The central server 102 decompresses and/or compiles the patient medical data and stores the patient medical data and patient information in storage 106. A processor 104 associated with the central server 102 controls the access to the patient medical data and patient information. The central server 102 transfers the patient medical data to the analysis workstation 124. Analysis workstation 124 receives the patient medical data from the central server 102 and analyzes the patient medical data. Based on this analysis, analysis workstation 124 generates the medical report and transfers the medical report to the central server 102. The central server 102 receives the medical report from analysis workstation 124 and stores the medical report.

Processor 104 controls access to the medical report. The central server 102 transmits the medical report to the remote computer 112. The remote computer 112 receives the medical report from the central server 102 and displays the medical report.

When introducing elements of the present invention or preferred embodiments thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above exemplary constructions and methods without departing from the scope of the invention, it is intended that all matter contained in the above description or shown in the accompanying drawings shall be interpreted as illustrative and not in a limiting sense. It is further to be understood that the method steps described herein are not to be construed as necessarily requiring their performance in the particular order discussed or illustrated. It is also to be understood that additional or alternative steps may be employed consistent with the present invention.

What is claimed is:

1. A central server for controlling the receipt and analysis of patient medical data and patient information, the central server comprising:
   a first communication interface for receiving the patient medical data and the patient information from one or more remote computers associated with the patient;
   a storage system remote with respect to at least some of the remote computers for receiving and storing the received patient medical data, patient information, and a medical report;
   a processor configured to associate patient medical data with patient information and for transferring the stored patient medical data in the storage system, said processor providing selective access to the patient medical data to one or more analysis workstations, each of the analysis workstations responsive to a medical specialist; and
   a second communication interface for transferring received and stored patient medical data to each of the analysis workstations, said communications interface transferring a particular received and stored patient medical data to a particular workstation in response to a selection of the particular received and stored medical data by the medical specialist associated with the particular analysis workstation, wherein said analysis workstations analyzes the patient medical data and prepares the medical report resulting from the analysis of the patient medical data, said second communication interface receiving from the analysis workstations the prepared medical report resulting from the analysis of the transferred patient medical data, wherein at least some of the analysis workstations are remote with respect to the central server and remote with respect to some of the remote computers;
   wherein the processor receives and transfers the medical report to the remote computer via the first communication interface.

2. The central server of claim 1, wherein the processor is further configured to host a web page and wherein a remote computer located remotely from the central server accesses the web page and transmits the patient medical data and patient information from the remote computers to the central server through the web page.

3. The central server of claim 2, wherein the central server is configured to receive segmented and compressed patient medical data from the remote computers which is configured to segment the patient medical data, compress the segmented patient medical data and transmit the segmented and compressed patient medical data and user information to the central server and wherein the central server is configured to decompress and recombine the received segmented and compressed patient medical data for storage and controlled access.

4. The central server of claim 1, wherein the first communication interface is configured for communication with a network and wherein each of the remote computers is configured for communication with the network such that central server receives the patient medical data and patient information transmitted by the remote computers via the network.

5. The central server of claim 4, further comprising a remote server configured for hosting a web page, wherein the remote server is operably connected to the network and wherein each of the remote computers is configured with a web browser for accessing the web page and transmitting the patient medical data and patient information through the web page to the remote server, and wherein the remote server transfers the received patient medical data and patient information to the central server via the first communication interface.

6. The central server of claim 1, wherein the central server is configured to receive patient medical data from the remote computers and wherein each of the remote computers and the central server are configured to communicate using a secure access that is a minimum of 128-bit secure socket layer connection.

7. The central server of claim 1, wherein one or more of the analysis workstations is responsive to one or more medical specialists and is associated with the central server, the central server securely transferring the patient medical data to each of the analysis workstations over the second communication interface; and wherein each of the analysis workstations is configured to analyze the medical data and create a medical report associated with the patient medical data, each of the analysis workstations transferring the medical report to the central server over the second communication interface.

8. The central server of claim 1, wherein the storage system comprises a database for storing and controlling access to the patient medical data, corresponding patient information, and the medical report.

9. The central server of claim 1, wherein the patient medical data is Holter data and wherein the medical report is a Holter analysis report.

10. A system for handling patient medical data over a network, comprising:
one or more remote computers configured to receive patient medical data from a medical sensor associated with the patient and configured to transfer the received patient medical data and patient information corresponding to the patient medical data;
a central server remote with respect to at least some of the remote computers configured to receive and store the transferred patient medical data and corresponding patient information and configured to control access to the patient medical data and its corresponding patient information, said central server configured to provide selective access to the patient medical data to one or more analysis workstations, each responsive to a medical specialist, wherein the analysis workstations analyzing the patient medical data and preparing a medical report resulting from the analysis of the patient medical data; and
wherein the one or more analysis workstations associated with the central server, each of the analysis workstations being operated by a medical specialist to select a particular received and stored patient medical data, and receive and analyze the selected patient medical data, each of the analysis workstations responsive to the medical specialist to create a medical report resulting from the analysis of the selected patient medical data, each of the analysis workstations transmitting the medical report to the central server, wherein at least some of the analysis workstations are remote with respect to the central server and remote with respect to the some of the remote computers;
wherein the central server is configured to receive from each of the analysis workstations the medical report resulting from the analysis of the patient medical data and corresponding patient information, and is configured to transmit the medical report to each of the remote computers.

11. The system of claim 10, further comprising a sensor configured to sense a parameter of the patient's body and store data corresponding to the sensed parameter as the patient medical data, the sensor being configured to transfer the patient medical data to each of the remote computers and each of the remote computers being configured to receive the transferred patient medical data.

12. The system of claim 11, wherein the sensor comprises a Holter monitor and the patient medical data comprises Holter data.

13. The system of claim 11, wherein the sensor and each of the remote computers are each configured with a USB interface wherein the sensor transfers the stored patient medical data to each of the remote computers via the USB interface.

14. The system of claim 11, wherein the sensor is equipped with a PCMCIA flashcard, the sensor storing the patient medical data on the PCMCIA flashcard and wherein each of the remote computers is configured to receive a PCMCIA flashcard and retrieve the patient medical data stored on the PCMCIA flashcard by the sensor.

15. The system of claim 11, wherein each of the remote computers is configured to receive the patient medical data from the sensor, segment the received patient medical data, compress the segmented patient medical data, and communicate the compressed patient medical data to the centralized server, the centralized server being configured to receive and store the compressed medical data.

16. The system of claim 10, wherein each of the remote computers is configured with a patient medical data acquisition, compression and transmission program for receiving patient medical data from a medical sensor, storing the patient medical data on each of the remote computers, compressing the medical data, and transferring the patient medical data from each of the remote computers to the central server.

17. The system of claim 10, wherein each of the remote computers is configured for communication via a network and for transmitting the patient medical data and its corresponding patient information to the central server via the network.

18. The system of claim 10, wherein the central server hosts a web page and wherein each of the remote computers is configured with a web browser for accessing the web page and transmitting the patient medical data from each of the remote computers to the central server via the web page.

19. The system of claim 10, further comprising a remote server hosting a web page which is remote from the central server and interconnected by a network, wherein each of the remote computers is configured with a web browser for accessing the web page and wherein the transfer of patient medical data and patient information from each of the remote computers is provided through the web page to the remote server and then transmitted by the remote server to the central server.

20. The system of claim 10, wherein the patient medical data is accessible by the medical specialist from each of the analysis workstations to perform analysis of the patient medical data, wherein each of the analysis workstations is configured to receive a medical report created by the medical specialist and analyze the medical data and transmit the medical report to the central server, and wherein the central server is configured to receive the medical report transmitted by each of the analysis workstations.

21. The system of claim 20, further comprising a display associated with each of the remote computers, wherein the central server is configured to transmit the medical report associated with the patient medical data to each of the remote computers and wherein each of the remote computers is configured to receive the medical report and display the medical report on the display.

22. A method of controlling the acquisition and analysis of patient medical data, the method comprising:
   receiving at a central server patient medical data and corresponding patient information from each of the remote computers, wherein the central server is remote with respect to at least some of the remote computers;
   controlling at the central server access to and analysis of the received patient medical data by providing secure access by one or more analysis workstations, wherein at least some of the analysis workstations are remote with respect to the central server and remote with respect to some of the remote computers, said one or more analysis workstations being operably interconnected by a network with the central server;
   transferring a particular received and stored patient medical data to a particular analysis workstation in response to a selection of the particular received and stored patient medical data by a medical specialist associated with the particular analysis workstation, wherein each of the analysis workstations is responsive to its associated medical specialist for analyzing the selected patient medical data and for creating a medical report associated with the received patient medical data;
   transferring the medical report to the central server from each of the analysis workstations;
   receiving from each of the analysis workstations the medical report associated with the patient medical data and corresponding patient information; and
   transmitting the medical report to each of the remote computers over the network.

23. A method according to claim 22, further comprising:
   hosting a web page by the central server;
   wherein receiving the patient medical data from each of the remote computers and transmitting the medical report to each of the remote computers are via the web page.

24. A method for managing the receipt and analysis of Holter monitor patient medical data, the method comprising:
   At a patient site remote with respect to analysis workstations, said analysis workstations analyzing the Holter monitor patient medical data:
      recording the Holter monitor patient medical data on a medical sensor;
      storing the Holter monitor patient medical data on a local storage medium;
      transmitting the stored patient medical data to a remote computer;
   At the remote computer site:
      creating patient information corresponding to the Holter monitor patient medical data;
      receiving the Holter monitor patient medical data from the medical sensor;
      storing the Holter monitor patient medical data on the remote computer;
      compressing the Holter monitor patient medical data;
      transmitting the compressed patient medical data and corresponding patient information to the central server;
   At a central server site remote with respect to the remote computer site:
      receiving the compressed patient medical data and corresponding patient information;
      decompressing the Holter monitor patient medical data;
      storing the Holter monitor patient medical data and patient information;
      controlling access to the Holter monitor patient medical data and patient information;
      transferring a particular patient medical data to a particular analysis workstation in response to a selection of the particular medical data by a medical specialist at the particular analysis workstation;
   At the particular analysis workstation site remote with respect to the central server site and remote with respect to the remote computer site and the patient site:
      receiving the selection from the medical specialist;
      receiving the particular patient medical data from the central server;
      analyzing the Holter monitor patient medical data;
      generating a medical report associated with the Holter monitor patient medical data;
      transferring the medical report to the central server;
   At the central sewer site:
      receiving the medical report from the analysis workstation;
      storing the medical report;
      controlling access to the medical report;
      transmitting the medical report to the remote computer;
   At the remote computer site:
      receiving the medical report from the central server; and
      displaying the medical report.

* * * * *